United States Patent [19]

Jautelat et al.

[11] Patent Number: 4,460,793
[45] Date of Patent: Jul. 17, 1984

[54] PREPARATION OF MONOCHLOROMETHYL KETONES

[75] Inventors: Manfred Jautelat, Burscheid; Dieter Arlt, Cologne; Gerhard Jäger, Leverkusen, all of Fed. Rep. of Germany

[73] Assignee: Bayer Aktiengesellschaft, Leverkusen, Fed. Rep. of Germany

[21] Appl. No.: 329,959

[22] Filed: Dec. 11, 1981

[30] Foreign Application Priority Data

Dec. 30, 1980 [DE] Fed. Rep. of Germany ....... 3049461

[51] Int. Cl.³ .............................................. C07C 45/42
[52] U.S. Cl. ............................... 568/405; 260/465 D; 568/306; 568/665; 568/362; 568/322; 568/393; 560/174
[58] Field of Search ............... 568/605, 322, 362, 386, 568/404, 405, 408, 393, 306; 560/174; 260/465 D

[56] References Cited

U.S. PATENT DOCUMENTS

| | | | |
|---|---|---|---|
| 1,829,869 | 11/1931 | Lazier | 568/362 |
| 2,988,537 | 6/1961 | Wiley | 568/405 |
| 3,277,068 | 10/1966 | Wall et al. | 568/655 |
| 3,294,820 | 12/1966 | Hudson et al. | 568/418 |
| 4,195,033 | 3/1980 | Punja | 568/386 |

FOREIGN PATENT DOCUMENTS

| | | | |
|---|---|---|---|
| 2716895 | 10/1978 | Fed. Rep. of Germany | 568/405 |
| 2716896 | 10/1978 | Fed. Rep. of Germany | 568/405 |

OTHER PUBLICATIONS

Sundberg, "The Chemistry of Indoles", Academic Press, pp. 164–171 (1970).
Russell, Aust. J. Chem., 1975, vol. 28 (11), pp. 2535–2538.
Russell, Chem. Abst., vol. 84, #17066h (1976).
Kuryla et al., J. Org. Chem., vol. 29, pp. 2773–2775 (1964).
Kuryla, J. Org. Chem., vol. 30, pp. 3926–3929 (1965).

*Primary Examiner*—James H. Reamer
*Attorney, Agent, or Firm*—Sprung, Horn, Kramer & Woods

[57] ABSTRACT

A process for the production of a monochloromethyl ketone of the formula

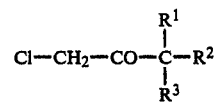

in which
R¹, R² and R³ each independently is a hydrogen atom or an optionally substituted alkyl, alkenyl, alkinyl or aryl radical, or
R¹ and R² together with the carbon atom to which they are attached form an optionally substituted carbocyclic ring, comprising reacting a 1,1-dichloroalkene of the formula

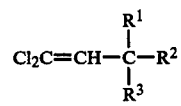

with a phenolate of the formula

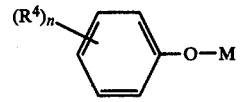

in which
R⁴ each independently is a halogen atom, a nitro group, or an optionally substituted alkyl, alkoxy or aryl radical,
n is 0, 1, 2 or 3, and
M is one equivalent of an alkali metal ion or alkaline earth metal ion, thereby to obtain a phenyl ether intermediate, and then subjecting the phenyl ether intermediate to an acid hydrolysis. The products are useful as intermediates in the synthesis of fungicides.

7 Claims, No Drawings

PREPARATION OF MONOCHLOROMETHYL KETONES

The present invention relates to an unobvious process for the preparation of certain partly known monochloromethyl ketones. Such ketones can be used as intermediate products for the synthesis of fungicidal azole derivatives.

It is already known that chloromethyl ketones are obtained by chlorination of methyl ketones (see Houben-Weyl, "Methoden der Org. Chemie (Methods of Organic Chemistry"), Volume 7/2c, page 2162, Georg Thieme Verlag Stuttgart (1977)). However, this process has the disadvantage that, in many cases, the products are not uniform, since a higher chlorination takes place in the 1-position and 3-position of the ketone, to give dichloro ketones and trichloro ketones. If further functional groups, which are sensitive to halogen, are present, such as a double bond in the ketone, this method can no longer be employed.

The present invention now provides a process for the production of a monochloromethyl ketone of the general formula

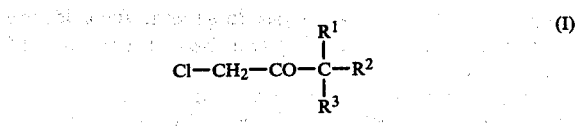

in which
R$^1$, R$^2$ and R$^3$ independently represent a hydrogen atom, or an alkyl, alkenyl, alkinyl or aryl radical which are optionally substituted in each case, or, in addition,
R$^1$ and R$^2$ together with the carbon atom to which they are attached form an optionally substituted carbocyclic ring, characterized in that a 1,1-dichloroalkene of the general formula

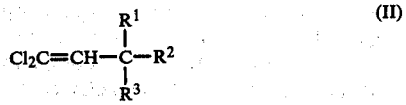

in which
R$^1$, R$^2$ and R$^3$ have the above meanings, is reacted with a phenolate of the general formula

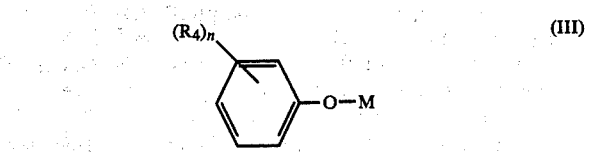

in which each
R$^4$ independently represents a halogen atom, or an alkyl, alkoxy and aryl radical which is optionally substituted in each case, or a nitro group,
n is 0, 1, 2 or 3 and
M represents one equivalent of an alkali metal ion or alkaline earth metal ion,
and the reaction product thereby obtained is then subjected to an acid hydrolysis.

The compounds of the general formula (I) are intermediate products for the preparation of plant protection agents.

According to previous knowledge, the reaction of vinylidene chloride with alcoholates leads to ketene acetals and orthoacetic acid esters (see J. Org. Chem. 29, 2773 (1964) and J. Org. Chem. 30, 3926 (1965)). In addition, it is known that the reaction of 1,1-dichloro-3,3-dimethyl-1,4-pentadiene and alcoholates leads to 3,3-dimethyl-4-pentenoic acid (see U.S. patent application Ser. No. 281,614, filed July 9, 1981, now pending. It is therefore exceptionally surprising that, according to the process according to the invention, the monochloromethyl ketones of the general formula (I) are obtained from 1,1-dichloroalkenes of the formula (II) and phenolates of the formula (III), and subsequent acid hydrolysis of the reaction products.

The process invented has a number of advantages. Thus, the starting materials, the 1,1-dichloroalkenes of the formula (II), are readily available, in a simple manner, from the addition of alkyl halides to vinylidene chloride, with Lewis acid catalysis (so-called Schmerling reaction, see J. Am. Chem. Soc. 74, 2885 (1952)). The reaction of the compounds of the formula (II) with the phenolates of the formula (III) proceeds with good yields, and, from the reaction products, the subsequent acid hydrolysis gives, in a selective manner, exclusively monochloromethyl ketones of the general formula (I). In this manner, unsaturated monochloromethyl ketones can also be prepared. The reaction according to the invention therefore represents an enrichment of the art.

If, for example, 1,1-dichloro-3,3-dimethyl-1,4-pentadiene and sodium phenolate are used as starting materials, the course of the reaction according to the present invention is illustrated by the following equation:

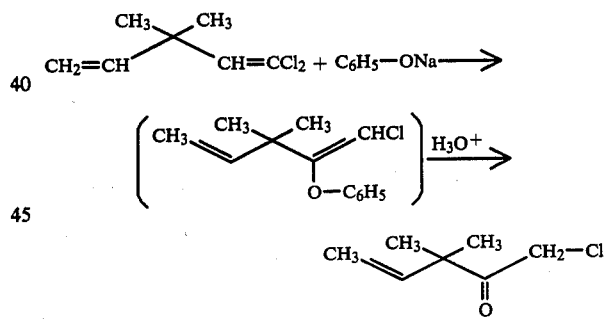

Preferred starting materials of formula (II) are those in which R$^1$ and R$^2$, which can be identical or different, represent a group selected from alkyl radicals with up to 4 carbon atoms, alkenyl or alkinyl radicals with, in each case, 2 to 4 carbon atoms, and phenyl radicals, the groups mentioned optionally being substituted by halogen, phenyl, alkoxy with up to 3 carbon atoms, or phenoxy, or R$^1$ and R$^2$ together, in addition, can also form an alkylene chain with 2 to 7 carbon atoms, and that chain can be optionally substituted by methyl groups and/or alkoxycarbonyl groups with 1 to 3 carbon atoms, R$^3$ represents a hydrogen atom, an alkyl radical with up to 10 carbon atoms, or an aryl radical with 6 to 10 carbon atoms, the alkyl radical or aryl radical optionally being substituted by halogen, nitro, alkoxy, alkyl, phenyl or cyano.

The following compounds may be mentioned individually as examples of the 1,1-dichloroalkenes, which are used, of the formula (II): 1,1-dichloro-3-methyl-1-butene, 1,1-dichloro-3,3-dimethyl-1-butene, 1,1-dichloro-3,3-dimethyl-1-pentene, 1,1-dichloro-3,3-dimethyl-1,4-pentadiene, 1,1-dichloro-3,3,4-trimethyl-1-pentene, 1,1-dichloro-3,3,5,5-tetramethyl-1-hexene, 1,1-dichloro-3,3-diethyl-1-pentene, 1,1-dichloro-3,3-dimethyl-1-octene, 1,1,4-trichloro-3,3-dimethyl-1-butene, 1,1,5-trichloro-3,3-dimethyl-1-pentene, 1,1,4-trichloro-3,3-dimethyl-1-pentene, 1,1-dichloro-3,3-dimethyl-5-fluoro-1-pentene, 1,1-dichloro-3,3-dimethyl-5-methoxy-1-pentene, 1,1-dichloro-3,3-dimethyl-5-(p-chlorophenoxy)-1-pentene, 1,1-dichloro-3-methyl-3-(p-chlorophenyl)-1-butene, 1,1-dichloro-1-butene, 1-(2,2-dichlorovinyl)-1-methyl-cyclohexane, 1-(2,2-dichlorovinyl)-1-ethyl-cyclopentane, 1-(2,2-dichlorovinyl)-1-methyl-cyclopropane, 1,1,4-trichloro-3,3-di-(chloromethyl)-1-butene, 1,1-dichloro-3-methyl-3-(2,4-dichlorophenyl)-1-butene, 1,1-dichloro-3,3-dimethyl-4-(2,4-dichlorophenyl)-1-butene, 1,1-dichloro-3,3-dimethyl-pent-1-ene-4-one and 1,1-dichloro-3-(2,4-dichlorophenyl)-1-propene.

The preparation of the 1,1-dichloroalkenes of the formula (II) is known, and is effected by addition of alkyl halides to vinylidene chloride in the presence of Lewis acid catalysts (see J. Am. Chem. Soc. 74, 2885 (1952)), with simultaneous cleavage of hydrogen halide.

Preferred phenolates of formula (III) which are further required as starting materials are those in which $R^4$ represents a chlorine or fluorine atom, an alkyl or alkoxy radical with, in each case, 1 to 3 carbon atoms, or a phenyl radical, n is 0, 1 or 2, the radical(s) $R^4$ being located in the 2-position, 3-position and/or 4-position, and M denotes a sodium ion or potassium ion.

The sodium salts and potassium salts of the following phenols may be mentioned as examples of the phenolates of formula (III): 4-chlorophenol, 2,4-dichlorophenol, 2,4,6-trichlorophenol, 4-methylphenol, 4-phenylphenol, 2,6-dimethylphenol, 3-methylphenol, 4-methoxyphenol, 4-fluorophenol, 4-bromophenol, 2-chlorophenol, 2-fluorophenol, 2-chloro-4-fluorophenol, 2,4-difluorophenol, 2-methyl-4-chlorophenol and 4-(p-chlorophenyl)-phenol.

The phenolates of the general formula (III) are compounds which are generally known and customary in the laboratory.

Any of the inert organic solvents are suitable diluents. Polar solvents (such as dimethylformamide, N-methyl-pyrrolidone, hexamethylphosphoric acid triamide, dimethylsulphoxide, 1,3-dimethyl-2-imidazolidone, tetramethylurea or sulpholane) are preferably used.

The reaction temperature can be varied within a wide range. In general, the reaction is carried out at a temperature between 50° and 250° C., preferably between 100° and 200° C. The reaction can be carried out under normal pressure in an open system as well as under pressure in an autoclave.

In carrying out the process according to the invention, 1 to 4 equivalents of phenolate of the formula (III), preferably 2 to 3 equivalents of anhydrous phenolate, are generally reacted with each equivalent of 1,1-dichloroalkene of the formula (II).

In a preferred embodiment of the process according to the present invention, the phenyl ether of the general formula

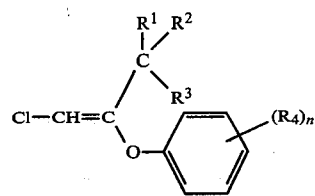

in which $R^1$, $R^2$, $R^3$, $R^4$ and n have the meanings given above, which is obtained as an intermediate from 1,1-dichloroalkene of the formula (II) and phenolate of the formula (III), is isolated and purified, for example by fractional distillation, before being subjected to acid hydrolysis, to give the compounds of the general formula (I).

The acid hydrolysis step is carried out, for example, with mineral acids (preferably sulphuric acid or hydrochloric acid) and/or with organic acids (such as formic acid, trifluoroacetic acid, oxalic acid, p-toluenesulphonic acid or methanesulphonic acid) at a temperature of from +20° to 150° C., preferably at 40° to 100° C. Alcohols (such as ethanol and methanol), ketones (such as acetone) or ethers (such as dioxane) are suitable solubilizers for the acid hydrolysis. In general, the acids are employed in excess, and they can also be present diluted with water.

Both reaction steps can be carried out not only separately but also successively in a "one-pot process," without the phenyl ether of the formula (IV) being isolated.

As already mentioned, the monochloromethyl ketones of the formula (I), which can be obtained according to the process according to the invention, are intermediate products for the preparation of fungicidal azole derivatives. Thus, for example by reacting these compounds with phenol or phenol derivatives (according to a so-called Williamson synthesis), the corresponding phenol ether ketones can be prepared, the latter can be reacted with halogenation agents to give the corresponding halogenated phenol ether ketones, and, finally, the corresponding azolyl compounds can be obtained by reaction with azoles (in this respect, see U.S. Pat. No. 4,229,580.) These compounds are known to have a good fungicidal activity (see U.S. Pat. No. 3,912,752 or the corresponding DE-PS No. 2,201,063).

The examples which follow illustrate the process according to the invention.

PREPARATION EXAMPLES

For the purpose of clarity, the phenol ethers, of the formula (IV), which are first obtained from 1,1-dichloroalkenes of the formula (II) and phenolates of the formula (III), are designated by A and subsequent compound number, for example A1 and A2. Compounds which are prepared in different ways, but are otherwise identical, are distinguished by lower case letters (in brackets) placed after those mentioned above, for example A1(a) and A1(b). The monochloromethyl ketones, of the formula (I), obtained by hydrolysis of the phenol ethers of the formula (IV), are designated by B and subsequent compound number, for example B1 and B2. Lower case letters in brackets, placed after these, distinguish between identical compounds prepared in different ways, as indicated above for the A compounds.

EXAMPLE A1(a)

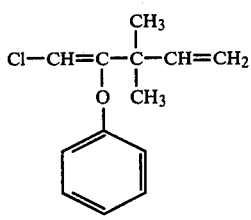

116 g (1 mol) of sodium phenolate and 82.5 g (0.5 mol) of 1,1-dichloro-3,3-dimethyl-1,4-pentadiene are heated under reflux in 500 ml of dimethylformamide for 8 hours. The solution is diluted with methylene chloride, and is extracted by shaking with dilute sodium hydroxide solution. After drying the methylene chloride phase over sodium sulphate, the solvent is stripped off in vacuo. 108.5 g (97% of theory) of crude product remain, and this product is distilled. 93.6 g (84% of theory) of 1-chloro-3,3-dimethyl-2-phenoxy-1,4-pentadiene pass over at a boiling point of 80° to 90° C./0.5 mm Hg.

NMR (CDCl$_3$): δ1.25 (s, 6H), 4.9–6.2 (—CH=CH$_2$), 5.85 (s, 1H), 6.8–7.4 (m, 5H).

Preparation of the precursors 3,3-Dimethyl-1,1,5-trichloro-1-pentene 20 g of aluminum chloride are dissolved in 2,300 g of 1,1-dichloroethene, while stirring and cooling to $-10°$ C. Thereupon, 1,286 g of 1,3-dichloro-3-methylbutane are added dropwise in the course of 3 hours, and simultaneously, at intervals of 15 minutes, further 3 g portions of aluminum chloride are added in measured amounts to the mixture, a reaction temperature of between 0° and +5° C. being maintained by cooling. After the end of the reaction, 60 ml of acetic acid are added dropwise to the reaction mixture. Thereafter, the product mixture is filtered over sodium sulphate, and is then metered into a distillation apparatus, the trough temperature being kept at 120° C., and a pressure of 1 mbar being maintained; the distillate is cooled and condensed by means of a dry ice/acetone mixture. The crude distillate is then fractionally distilled in vacuo in a Vigreux column. 1,650 g of 3,3-dimethyl-1,1,5-trichloro-1-pentene of boiling point 59° to 63° C./0.1 mm Hg are obtained. 1,1-Dichloro-3,3-dimethyl-1,4-pentadiene 201.5 g (1 mol) of 3,3-dimethyl-1,1,5-trichloro-1-pentene are slowly added dropwise into 1 l of quinoline, and 83 g potassium carbonate at 225° to 230° C., and distillate is simultaneously taken off via the head of a column. The temperature in the flask is raised to the boiling point of the quinoline, and a total of 126 g of distillate is isolated, the distillate again being fractionally distilled. 121 g (73% of theory) of 1,1-dichloro-3,3-dimethyl-1,4-pentadiene are obtained at a boiling point of 59°–53° C./20 mm Hg.

EXAMPLE B1(a)

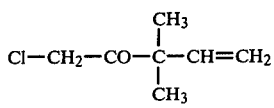

57 g (0.256 mol) of 1-chloro-3,3-dimethyl-2-phenoxy-1,4-pentadiene (see Example A1(a)) are warmed to 40° C. in a mixture of 250 ml of formic acid and 50 ml of concentrated hydrochloric acid, during the course of 1 hour. The mixture is then diluted with 400 ml of methylene chloride and ice, and is three times extracted by shaking with 2N sodium hydroxide solution. After drying the methylene chloride phase over sodium sulphate, the solvent is removed. 36 g of product (96% of theory) remain, and this product is distilled. 32.2 g (86% of theory) of 1-chloro-3,3-dimethyl-pent-4-en-2-one are obtained at a boiling point of 81°–84° C./24 mm Hg.

NMR (CDCl$_3$): δ1.3 (s, 6H), 4.35 (s, 2H), 5.0–6.2 (—CH=CH$_2$)

EXAMPLE A1(b)

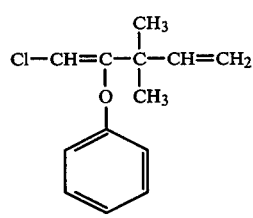

23.2 g (0.2 mol) of sodium phenolate and 16.5 g (0.1 mol) of 1,1-dichloro-3,3-dimethyl-1,4-pentadiene are heated to 180° C. in 100 ml of N-methylpyrrolidone, during the course of 10 hours. The working-up corresponding to Example A1(a) yields 20.5 g (92% of theory) of 1-chloro-3,3-dimethyl-2-phenoxy-1,4-pentadiene.

EXAMPLE A1(c)

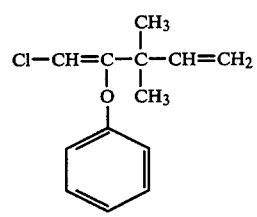

26.4 g (0.2 mol) of potassium phenolate and 16.5 g (0.1 mol) of 1,1-dichloro-3,3-dimethyl-1,4-pentadiene are heated to 180° C. in 100 ml of hexamethylphosphoric acid triamide, during the course of 6 hours. The working-up analogous to Example A1(a) yields 15.8 g (71% of theory) of 1-chloro-3,3-dimethyl-2-phenoxy-1,4-pentadiene.

EXAMPLE B1(b)

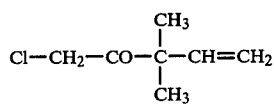

22.2 g (0.1 mol) of 1-chloro-3,3-dimethyl-2-phenoxy-1,4-pentadiene are heated under reflux in 200 ml of ethanol and 50 ml of concentrated hydrochloric acid, during the course of 5 hours. The working-up according to Example B1(a) leads to 12 g of 1-chloro-3,3-dimethyl-pent-4-en-2-one, which are 82% of theory.

EXAMPLE B1(c)

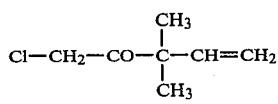

4.44 g (20 mmols) of 1-chloro-3,3-dimethyl-2-phenoxy-1,4-pentadiene are warmed to 100° C. in 20 ml of dioxane and 10 ml of 50% sulphuric acid, during the course of 6 hours. The working-up according to Example B1(a) yields 2.1 g of 1-chloro-3,3-dimethyl-pent-4-en-2-one, which are 72% of theory.

EXAMPLE B1(d)

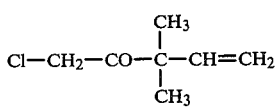

22.2 g (0.1 mol) of 1-chloro-3,3-dimethyl-2-phenoxy-1,4-pentadiene are heated under reflux in 100 ml of acetic acid, during the course of 4 hours. The working-up corresponding to Example B1(a) yields 11.9 g of 1-chloro-3,3-dimethyl-pent-4-en-2-one, which are 81% of theory.

EXAMPLE B1(e)

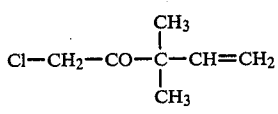

22.2 g (0.1 mol) of 1-chloro-3,3-dimethyl-2-phenoxy-1,4-pentadiene are heated under reflux with 100 ml of 15% strength hydrochloric acid. After the working-up according to Example B1(a), 11.4 g of 1-chloro-3,3-dimethyl-pent-4-en-2-one are obtained, which are 78% of theory.

EXAMPLE A2(a)

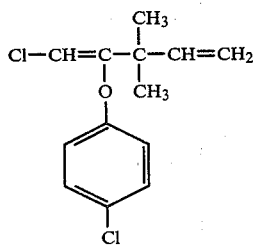

51.4 g (0.4 mol) of p-chlorophenol are reacted, in 300 ml of dimethylformamide, with 80 ml of 30% strength sodium methylate solution (0.4 mol), and the solvent is then stripped off at 30 mbar. 33 g (0.2 mol) of 1,1-dichloro-3,3-dimethyl-1,4-pentadiene are then added to the mixture, and the latter is heated under reflux during the course of 9 hours. The working-up is according to Example A1(a). The distillation at a boiling point of 122°–130° C./0.2 mm Hg yields 44.8 g of 1-chloro-3,3-dimethyl-2-(p-chlorophenoxy)-1,4-pentadiene, which are 87% of theory.

EXAMPLE B1(f)

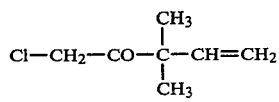

5.16 g (20 mmols) of 1-chloro-3,3-dimethyl-2-(p-chlorophenoxy)-1,4-pentadiene, prepared according to Example A2(a) above, are warmed to 50° C. in a mixture of 20 ml of formic acid and 2 ml of concentrated hydrochloric acid, during the course of 2 hours. The working-up corresponding to Example B1(a) yields 2.47 g of 1-chloro-3,3-dimethyl-pent-4-en-2-one, which are 84% of theory.

EXAMPLE A3(a)

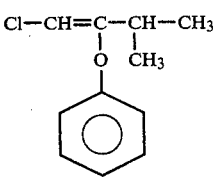

139 g (1 mol) of 1,1-dichloro-3-methyl-1-butene are slowly added dropwise at 150° C. to a suspension of 232 g (2 mols) of sodium phenolate in 1 l of dimethylformamide, and the mixture is heated under reflux during the course of 8 hours. After working-up according to Example A1(a), 165 g of 1-chloro-3-methyl-2-phenoxy-1-butene, which are 84% of theory, are obtained at a boiling point of 80°–86° C./0.3 mm Hg.

NMR (CDCl$_3$): δ1.05 (d, J=6.5 Hz, 6H), 2.45 (h, J=6.5 Hz, 1H), 5.75 (s, 1H), 6.8–7.4 (m, 5H).

EXAMPLE B2(a)

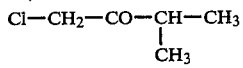

146.7 g (0.75 mol) of 1-chloro-3-methyl-2-phenoxy-1-butene, prepared according to Example A3(a) above, are warmed to 50° C. with 375 ml of formic acid and 27.5 ml of concentrated hydrochloric acid, during the course of 1 hour. The working-up according to Example B1(a) leads to 70.9 g of 1-chloro-3-methyl-2-butanone of boiling point 50°–51° C./20 mm Hg, which are 78% of theory.

NMR (CDCl): δ1.15 (d, H=6.5 Hz, 6H), 2.9 (h, J=6.5 Hz, 1H), 4.25 (s, 2H).

EXAMPLE A4(a)

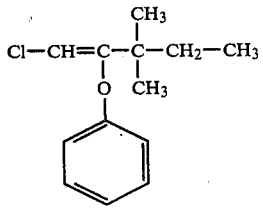

23.2 g (0.2 mol) of sodium phenolate are heated under reflux with 18.6 g (0.11 mol) of 1,1-dichloro-3,3-dimethyl-1-pentene in 100 ml of dimethylformamide, during the course of 20 hours. After the customary working-up, 20.4 g of 1-chloro-3,3-dimethyl-2-phenoxy-1-pentene are distilled at a boiling point of 104° C./0.2 mm Hg, which are 84% of theory.

NMR (CDCl₃): δ0.85 (t, J=7 Hz, 3H), 1.05 (s, 6H), 1.5 (q, J=7 Hz, 2H), 5.9 (s, 1H), 6.7-7.3 (m, 5H).

EXAMPLE B3(a)

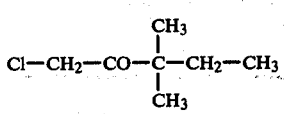

341 g (1.52 mols) of 1-chlor-3,3-dimethyl-2-phenoxy-1-pentene, prepared according to Example A4(a) above, are warmed to 80° C. in 500 ml of formic acid and 100 ml of concentrated hydrochloric acid, during the course of 2 hours. The customary working-up according to Example B1(a) leads to 183 g of 1-chloro-3,3-dimethyl-2-pentanone of boiling point 75°-83° C./20 mm Hg, which are 81% of theory.

NMR (CDCl₃): δ0.8 (t, J=7 Hz, 3H), 1.2 (s, 6H), 1.6 (q, J=7 Hz, 2H), 4.35 (s, 2H).

EXAMPLE A5(a)

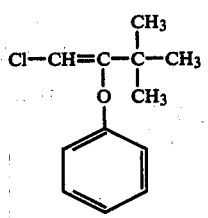

16.5 g (0.108 mols) of 1,1-dichloro-3,3-dimethyl-1-butene are heated under reflux with 23.2 g (0.2 mol) of sodium phenolate in 100 ml of dimethylformamide, during the course of 12 hours. The customary working-up according to Example A1(a) yields, with distillation at a boiling point of 80° C./0.5 mm Hg, 22.3 g of 1-chloro-3,3-dimethyl-2-phenoxy-1-butene.

NMR (CDCl₃): δ1.15 (s, 9H), 5.9 (s, 1H), 6.9-7.5 (m, 5H).

EXAMPLE B4(a)

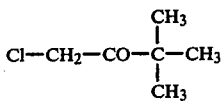

21 g (0.1 mol) of 1-chloro-3,3-dimethyl-2-phenoxy-1-butene, prepared according to Example A5(a) above, are warmed to 80° C. with 20 ml of formic acid and 2 ml of concentrated hydrochloric acid, during the course of 1 hour. The customary working-up according to Example B1(a) leads to 12.1 g of 1-chloro-3,3-dimethyl-2-butanone of boiling point of 70° C./24 mm Hg, which are 90% of theory.

NMR (CDCl₃): δ1.2 (s, 9H), 4.45 (s, 2H).

EXAMPLE A6(a)

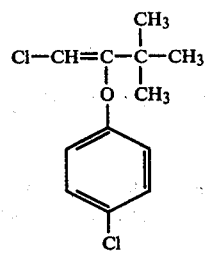

26 g (0.2 mol) of p-chlorophenol are reacted, in 150 ml of dimethylformamide, with 40 ml of 30% sodium methylate solution (0.2 mol), and the mixture is freed at 20 mbar from methanol. After 15.3 g (0.1 mol) of 1,1-dichloro-3,3-dimethyl-1-butene have been added to the mixture, the latter is heated under reflux during the course of 18 hours. The distillation, after working-up according to Example A1(a), leads to 21 g of 1-chloro-3,3-dimethyl-2-(p-chlorophenoxy)-1-butene of boiling point 120°-128° C./0.15 mm Hg.

NMR (CDCl₃): δ1.15 (s, 9H), 5.9 (s, 1H), 6.8-7.35 (m, 4H).

EXAMPLE A7(a)

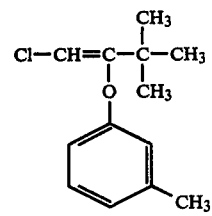

Analogously to Example A6(a), 0.2 mol of 3-methylphenol and 0.1 mol of 1,1-dichloro-3,3-dimethyl-1-butene are reacted to give 19.6 g of 1-chloro-3,3-dimethyl-2-(3'-methylphenoxy)-1-butene of boiling point 95°-100° C./0.7 mm Hg. The yield is 87% of theory.

NMR (CDCl₃): δ1.15 (s, 9H), 2.3 (s, 3H), 5.85 (s, 1H), 6.6-7.3 (m, 4H).

EXAMPLE A8(a)

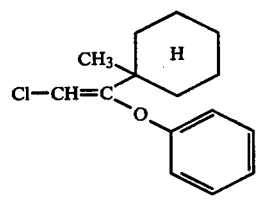

19.3 g (0.1 mol) of 1-(2',2'-dichlorovinyl)-1-methylcyclohexane and 23.2 g (0.2 mol) of sodium phenolate are heated under reflux in 100 ml of dimethylformamide, during the course of 10 hours. The customary working-up (see A1(a)) leads to 18.6 g of 1-chloro-2-(1'-methylcyclohexyl)-2-phenoxyethylene of boiling point 100° C./0.03 mm Hg. The yield is 74% of theory.

NMR (CDCl₃): δ1.15 (s, 3H), 1.1-2.2 (m, 10H), 5.85 (s, 1H), 6.8-7.4 (m, 5H).

EXAMPLE B5(a)

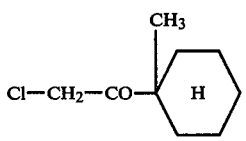

62 g (0.25 mol) of 1-chloro-2-(1'-methylcyclohexyl)-2-phenoxy-ethylene, prepared according to A8(a) above, are heated to 80° C. in 300 ml of formic acid and 60 ml of concentrated hydrochloric acid during the course of 2 hours. After the customary working-up (see B1(a)), 39.6 g of 1-chloroacetyl-1-methyl-cyclohexane of boiling point 115° C./20 mm Hg are obtained. Yield 92% of theory.

NMR (CDCl$_3$): δ1.2 (s, 3H), 1.2–2.2 (m, 10H), 4.2 (s, 2H).

Further, the following compounds were also prepared in a corresponding manner, as indicated in the above examples:

| Example No. | Structure | Boiling point (mm Hg/°C.) |
|---|---|---|
| A9(a) | Cl—CH=CH—C(CH$_3$)(CH$_3$)(C$_6$H$_5$)—O—C$_6$H$_5$ | 0.15/153–156° |
| B6(a) | Cl—CH$_2$—CO—C(CH$_3$)(CH$_3$)(C$_6$H$_5$) | 0.3/130–139° |
| A10(a) | Cl—CH=C(O—C$_6$H$_5$)—C(CH$_3$)$_2$—CH$_2$—CH$_2$F | 0.1/120–128° |
| B7(a) | Cl—CH$_2$—CO—C(CH$_3$)$_2$—CH$_2$—CH$_2$—F | 20/50–51° |
| A11(a) | Cl—CH=C(O—C$_6$H$_5$)—C(CH$_3$)$_2$—CH$_2$—CH$_2$—O—C$_6$H$_5$ | 0.1/150–168° |
| B8(a) | Cl—CH$_2$—CO—C(CH$_3$)$_2$—CH$_2$—CH$_2$—O—C$_6$H$_5$ | 0.2/150–155° |
| A12(a) | Cl—CH=C(O—C$_6$H$_5$)—CH[C(CH$_3$)$_2$]CH—CO—O—CH$_3$ | 0.15/130–150° |
| B9(a) | Cl—CH$_2$—CO—CH[C(CH$_3$)$_2$]CH—CO—O—CH$_3$ | 0.1/90° |
| A13(a) | Cl—CH=C(O—C$_6$H$_5$)—C(CH$_3$)(CH$_3$)—CH(CH$_3$)(CH$_3$) | 0.04/94–96° |
| B10(a) | Cl—CH$_2$—CO—C(CH$_3$)(CH$_3$)—CH(CH$_3$)(CH$_3$) | 20/97–105° |
| A14 | Cl—CH=C(O—C$_6$H$_5$)—C(CH$_3$)$_2$—(2,4-Cl$_2$C$_6$H$_3$) | 0.07/160–180° |

-continued

| Example No. | | Boiling point (mm Hg/°C.) |
|---|---|---|
| B11 | Cl—CH$_2$—CO—C(CH$_3$)$_2$—C$_6$H$_3$Cl$_2$ | 0.08/145–155° |
| A15 | Cl—CH=C(OC$_6$H$_5$)—C(CH$_3$)$_2$—C(CH$_3$)$_3$ | 0.5/123–128° |
| B12 | Cl—CH$_2$—CO—C(CH$_3$)$_2$—C(CH$_3$)$_3$ | 14/105–110° |
| A16 | Cl—CH=C(OC$_6$H$_5$)—C(C$_2$H$_5$)$_3$ | 0.06/105–115° |
| B13 | Cl—CH$_2$—CO—C(C$_2$H$_5$)$_3$ | 18/102–107° |
| B14 | Cl—CH$_2$—CO—C(CH$_3$)$_2$—CH$_2$—CH$_2$—O—C$_6$H$_3$Cl$_2$ | Mp. 55–58° |

The compounds according to Examples A1, A2, A3, A4, A8, A10, A11, A12, A13, A14, A15, A16 and B1, B3, B5, B7, B8, B9, B10, B11, B12, B13, B14 are new.

Compound B1 is a new compound of special interest as an intermediate product for the preparation of fungicidally active products which can be prepared as described above.

It will be understood that the specification and examples are illustrative but not limitative of the present invention and that other embodiments within the spirit and scope of the invention will suggest themselves to those skilled in the art.

We claim:

1. A process for the production of monochloromethyl ketone of the formula

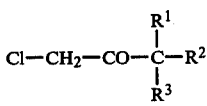

in which

R$^1$, R$^2$ and R$^3$ each independently is a hydrogen atom or an (optionally substituted) alkyl, alkenyl or alkinyl radical with up to 4 carbon atoms or an aryl radical, any of the foregoing being optionally substituted by halogen, phenyl, alkoxy with up to 3 carbon atoms or phenoxy, or R$^1$ and R$^2$ together with the carbon atom to which they are attached form a carbocyclic ring optionally substituted by methyl groups and/or alkoxycarbonyl groups with 1 to 3 carbon atoms, comprising reacting a 1,1-dichloroalkene of the formula

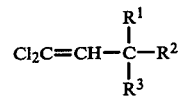

with a phenolate of the formula

in which

R$^4$ each independently is a halogen atom, a nitro group, or an alkyl or alkoxy radical with 1 to 3 carbon atoms, or a phenyl radical, n is 0, 1, 2, or 3, and M is one equivalent of an alkali metal ion or alkaline earth metal ion, at from about 50° to 250° C. thereby to obtain a phenyl ether intermediate, and then subjecting the phenyl ether intermediate to an acid hydrolysis.

2. A process according to claim 1, wherein the reaction is carried out at a temperature between about 100° and 200° C.

3. A process according to claim 1, wherein the phenyl ether is of the formula

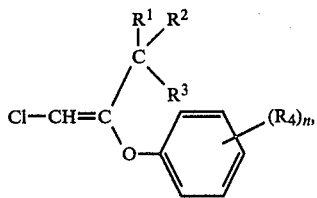

is isolated and is purified before being subjected to the acid hydrolysis.

4. A process according to claim 1, in which:
$R^1$ and $R^2$ each independently is an alkyl, alkenyl or alkinyl radical with up to 4 carbon atoms, or a phenyl radical, the radicals optionally being substituted by halogen, phenyl, alkoxy with up to 3 carbon atoms, or phenoxy, or $R^1$ and $R^2$ together can form an alkylene chain with 2 to 7 carbon atoms optionally substituted by methyl groups and/or alkoxycarbonyl groups with 1 to 3 carbon atoms, and $R^3$ is a hydrogen atom, or an alkyl radical with up to 10 carbon atoms or an aryl radical with 6 to 10 carbon atoms, either optionally substituted by halogen, nitro, alkoxy, alkyl, phenyl or cyano.

5. A process according to claim 1, in which:
$R^4$ is a chlorine or fluorine atom, an alkyl or alkoxy radical with 1 to 3 carbon atoms, or a phenyl radical, the radical $R^4$ being located in the 2-position, 3-position and/or 4-position, n is 0, 1 or 2, and M is a sodium or potassium ion.

6. A process according to claim 4, in which:
$R^4$ is a halogen atom, a nitro group, or an optionally substituted alkyl, alkoxy or aryl radical, n is 0, 1, 2 or 3, and M is one equivalent of an alkali metal ion or alkaline earth metal ion, the reaction is carried out at a temperature between about 100° and 200° C., and the phenyl ether intermediate is isolated and purified before being subjected to the acid hydrolysis.

7. A process according to claim 6, wherein $R^1$ and $R^3$ are methyl and $R^2$ is vinyl.

* * * * *